(12) United States Patent
Schrader

(10) Patent No.: US 6,727,452 B2
(45) Date of Patent: Apr. 27, 2004

(54) SYSTEM AND METHOD FOR REMOVING DEFECTS FROM CITRUS PULP

(75) Inventor: Gregory W. Schrader, Lakeland, FL (US)

(73) Assignee: FMC Technologies, Inc., Chicago, IL (US)

(*) Notice: Subject to any disclaimer, the term of this patent is extended or adjusted under 35 U.S.C. 154(b) by 173 days.

(21) Appl. No.: 10/036,636

(22) Filed: Jan. 3, 2002

(65) Prior Publication Data

US 2003/0124217 A1 Jul. 3, 2003

(51) Int. Cl.$^7$ ................................................ B07C 5/00
(52) U.S. Cl. ........................ 209/576; 209/577; 209/588; 209/639; 382/110
(58) Field of Search ................... 382/110; 252/458.1, 252/459.1; 356/317; 209/576, 577, 588, 639, 644, 652

(56) References Cited

U.S. PATENT DOCUMENTS

| | | | |
|---|---|---|---|
| 3,011,634 A | | 12/1961 | Hutter et al. |
| 3,628,657 A | * | 12/1971 | Billett ........................ 209/579 |
| 3,756,404 A | | 9/1973 | King et al. |
| 3,930,994 A | * | 1/1976 | Conway et al. ............. 209/579 |
| 4,035,518 A | | 7/1977 | Carmona et al. |
| 4,139,651 A | | 2/1979 | Sekiguchi |
| 4,324,335 A | * | 4/1982 | Conway et al. ............. 209/586 |
| 4,454,029 A | | 6/1984 | Codding |
| 4,718,558 A | | 1/1988 | Castaneda |
| 4,738,175 A | | 4/1988 | Little et al. ..................... 83/71 |
| 4,795,651 A | | 1/1989 | Henderson et al. |
| 4,849,625 A | | 7/1989 | Camerini Porzi |
| 4,889,793 A | | 12/1989 | Taniguchi et al. |
| 4,942,051 A | | 7/1990 | Sardisco |
| 4,973,485 A | | 11/1990 | Rich |
| 5,000,569 A | | 3/1991 | Nylund ........................ 356/237 |
| 5,085,325 A | | 2/1992 | Jones et al. .................. 209/580 |
| 5,260,086 A | | 11/1993 | Downton et al. |
| 5,269,218 A | | 12/1993 | Alexander et al. |
| 5,273,166 A | | 12/1993 | Sawamura |
| 5,297,667 A | | 3/1994 | Hoffman et al. |
| 5,305,894 A | * | 4/1994 | McGarvey ................... 209/580 |
| 5,335,791 A | | 8/1994 | Eason ........................ 209/588 |
| 5,440,127 A | | 8/1995 | Squyres .................... 250/341.8 |
| 5,443,164 A | * | 8/1995 | Walsh et al. ................. 209/580 |
| 5,703,784 A | | 12/1997 | Pearson |
| 5,732,147 A | * | 3/1998 | Tao ............................ 382/110 |
| 5,791,497 A | * | 8/1998 | Campbell et al. ........... 209/577 |
| 5,845,002 A | * | 12/1998 | Heck et al. .................. 382/110 |
| 6,312,753 B1 | | 11/2001 | Kealey et al. |
| 2002/0061350 A1 | * | 5/2002 | Thomas et al. .............. 426/482 |

FOREIGN PATENT DOCUMENTS

| | | | |
|---|---|---|---|
| DE | 195 48 692 A1 | 6/1997 | ............. A23J/1/09 |
| WO | WO 00/58035 | 5/2000 | |

* cited by examiner

Primary Examiner—Donald P. Walsh
Assistant Examiner—Joseph Rodriguez
(74) Attorney, Agent, or Firm—Allen, Dyer, Doppelt, Milbrath & Gilchrist, P.A.

(57) ABSTRACT

A system and method of the present invention removes defects from citrus pulp. An advancing mechanism advances citrus pulp along a predetermined path of travel into an inspection zone. A citrus pulp imager is positioned at the inspection zone and acquires image data of the citrus pulp. A processor is operatively connected to the citrus pulp imager and receives the image data and processes the image data to determine defects within the citrus pulp. A rejection mechanism rejects any citrus pulp determined to be defective.

17 Claims, 6 Drawing Sheets

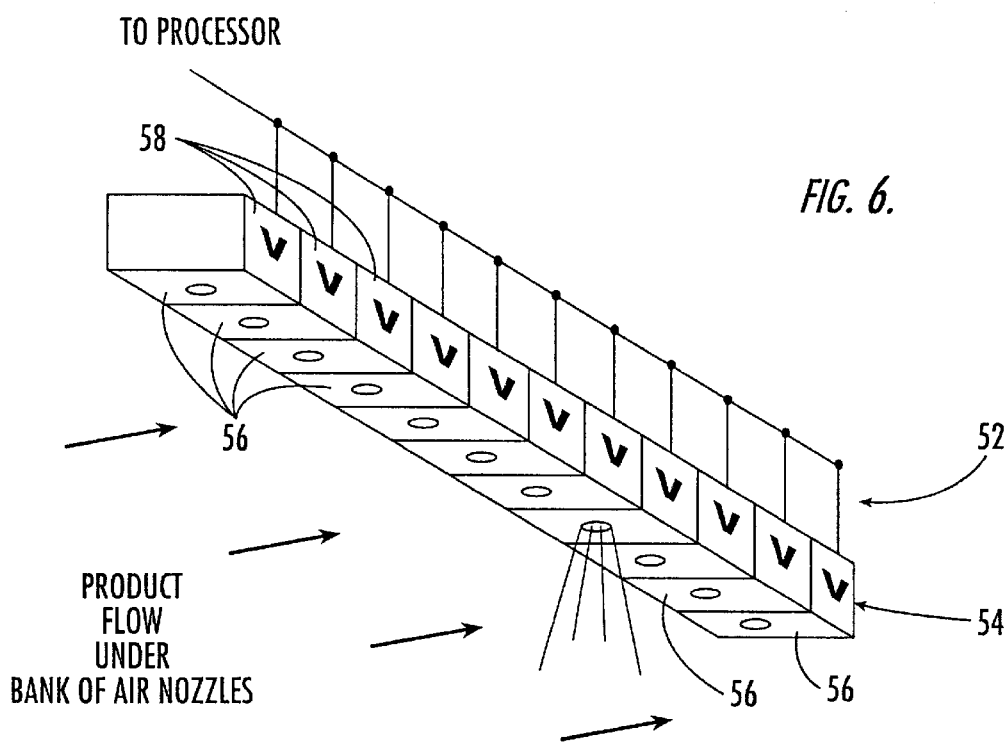
FIG. 6.
PRODUCT FLOW UNDER BANK OF AIR NOZZLES
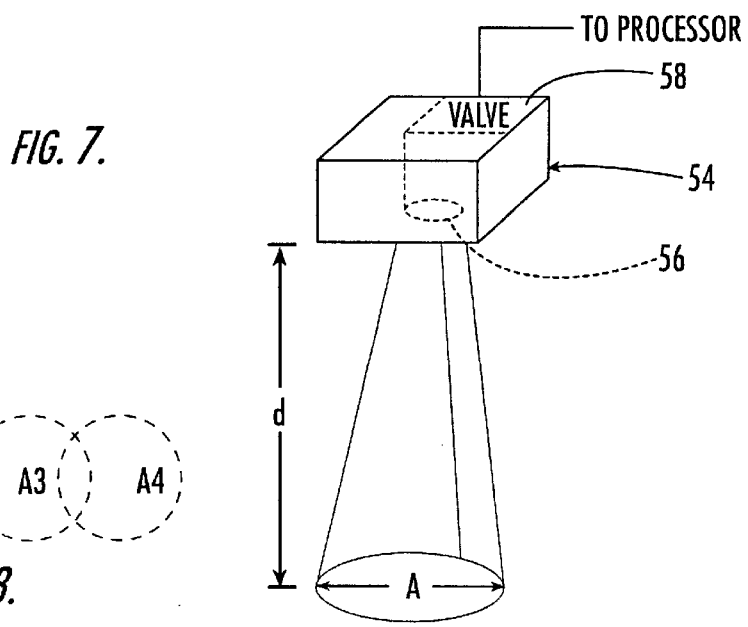
FIG. 7.
FIG. 8.

SYSTEM AND METHOD FOR REMOVING DEFECTS FROM CITRUS PULP

FIELD OF THE INVENTION

This invention relates to citrus pulp processing, and more particularly, this invention relates to a system and method for removing defects from citrus pulp.

BACKGROUND OF THE INVENTION

Citrus pulp is separated from juice typically by processing the citrus pulp in a juice extractor, which strains out most of the seeds and membranes through a strainer tube to produce a fine citrus pulp and juice product. This juice product advances and is further processed at a juice finisher for separating citrus pulp from the juice. At this point in the processing, the pulp is somewhat "clean," after having been broken up into smaller citrus pulp pieces as a result of processing through the strainer tube at the juice extractor.

It is desirable in some cases to produce a larger pulp sack in a premium pulp system by recovering pulp sacks that are more intact. For example, this citrus pulp can be added back to the juice to form a final product, e.g., a pulpy orange juice, or the citrus pulp can be collected separately, cleaned and pasteurized, and shipped to customers that package their own juice or sell citrus pulp wholesale.

There are also an increasing number of customers that collect citrus pulp as a byproduct to sell for additional revenue. Thus, an increasing number of customers require citrus pulp to be processed with large and intact pulp sacks. One way to accomplish this goal is to design a juice extractor having larger openings in the strainer tube. Although larger, intact pulp sacks would be processed, the use of larger openings in a strainer tube has drawbacks, however, because undesired material and citrus pulp defects could pass through the slots.

One prior art solution is a premium pulp system using a juice extractor, followed by processing at a juice finisher, and further processing for cleaning in a fluidized bed cyclone in which pulp and juice are processed together to separate components out by gravity. The design of the fluidized bed cyclone allows fluid to enter in tangentially and spin, with 20–30% of pulpy juice ejected from the bottom and 70% ejected from the top as a pulp and juice product. In a preferred mode of operation, small seeds and peel particles are ejected from the bottom portion of the fluidized bed cyclone.

There are some drawbacks to this system because the defects that are processed as part of the juice and citrus pulp are unacceptable to many customers. These defects may include discolored pulp, peel or portions of peel, albedo or portions of albedo, seeds, portions of seeds, black specks, mold, and non-citrus material such as insects, insect larvae or insect parts. Different customers have different specifications concerning these defects, depending on the citrus pulp defect, category of juice, and customer end use. In some cases, defects are unacceptable at any level, such as insect larvae.

SUMMARY OF THE INVENTION

It is therefore an object of the present invention to provide a system and method for removing defects from citrus pulp that advantageously overcome the prior art drawbacks identified above.

In accordance with the present invention, a citrus pulp imager acquires image data of the citrus pulp at an inspection zone that receives citrus pulp advancing along a predetermined path of travel. A processor is operatively connected to the citrus pulp imager for receiving the image data and processing the image data to determine defects within the citrus pulp. A rejection mechanism rejects any citrus pulp determined to be defective.

In one aspect of the present invention, a light source illuminates the citrus pulp at the inspection zone. A camera is located at the inspection zone and acquires images of the citrus pulp. This camera can be a line-scan camera, CCD camera, or other imaging camera or similar mechanism that is operative for acquiring images of citrus pulp. A light source illuminates the citrus pulp and is operative at a predetermined range of wavelengths for highlighting defects to be illuminated. In one aspect of the invention, the wavelengths are such as to cause defects to fluoresce.

In yet another aspect of the present invention, the advancing mechanism includes a belt conveyor, nozzle or translucent material through which citrus pulp is advanced and can be imaged. The rejection mechanism could include a mechanical diverter that diverts any citrus pulp determined to be defective from the path of travel, or an air nozzle that blows a jet of air onto citrus pulp determined to be defective to eject or divert the defective citrus pulp from the path of travel. In one aspect of the present invention, the processor is operative for determining defects in citrus pulp, including but not limited to, discolored pulp, peel or portions of peel, albedo or portions of albedo, seeds, portions of seeds, black specks, mold, or non-citrus material such as insects, insect larvae or insect parts.

BRIEF DESCRIPTION OF THE DRAWINGS

Other objects, features and advantages of the present invention will become apparent from the detailed description of the invention which follows, when considered in light of the accompanying drawings in which:

FIG. 6 is a fragmentary, isometric view of a bank of air valves and air nozzles for blowing air onto citrus pulp determined to be defective and diverting a desired portion of the advancing citrus pulp determined to be defective from the path of travel.

FIG. 7 is a fragmentary, isometric view of a single air nozzle that blows air onto a given area "A" at a distance "D" for diverting citrus pulp from the path of travel.

FIG. 8 is a fragmentary drawing view that shows the overlap of areas "A" from each air nozzle.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
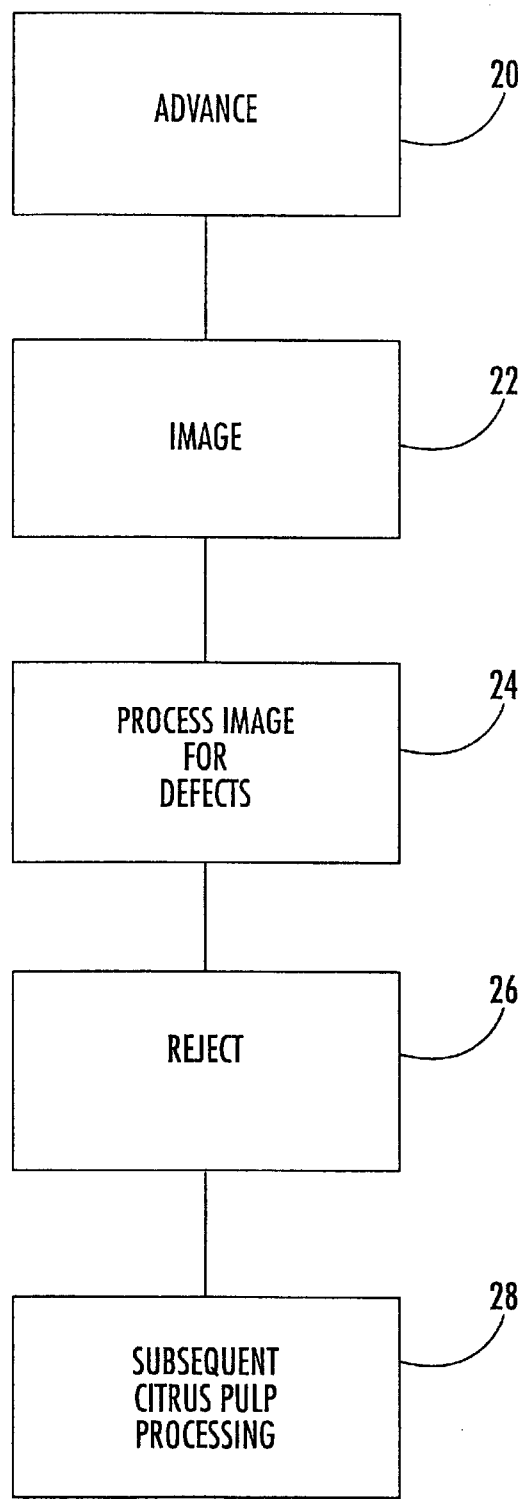
FIG. 1 is a high level flow chart showing the basic sequence of operation for the system and method of removing defects from citrus pulp in accordance with one aspect of the present invention.

The present invention advantageously overcomes the disadvantages of prior art citrus pulp defect removal systems by using citrus pulp imaging during processing and removing defects from the citrus pulp in an economical and advanced manner without harming the citrus pulp and damaging intact pulp sacks. FIG. 1 illustrates a basic block diagram showing key steps in the system and method for removing defects from citrus pulp in accordance with one aspect of the present invention. An advancing mechanism advances citrus pulp along a predetermined path of travel into an inspection zone in a first step (Block 20). A citrus pulp imager, such as a camera, is positioned at the inspection zone and acquires image data of the citrus pulp (Block 22). A processor is operatively connected to the citrus pulp imager and receives the image data and processes the image data to determine defects within the citrus pulp (Block 24). A rejection mechanism is positioned along the predetermined path of travel and rejects any citrus pulp determined to be defective (Block 26). Citrus pulp is subsequently processed (Block 28).

Figure 2:
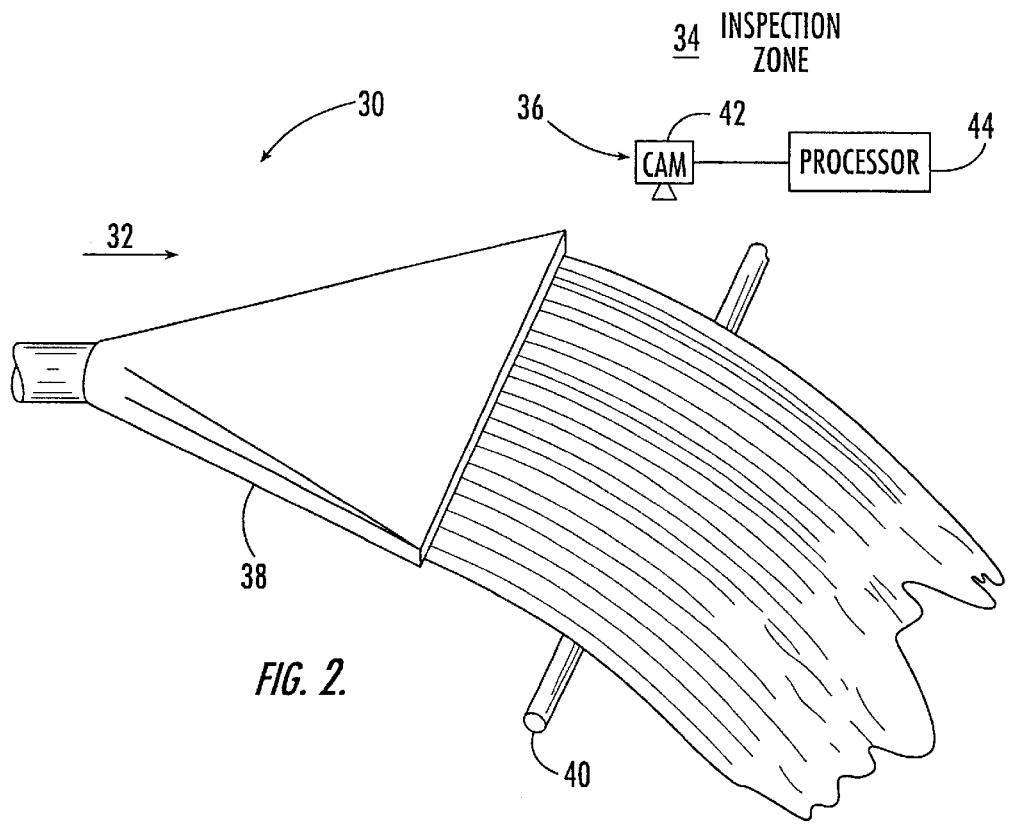
FIG. 2 is a fragmentary, isometric view of an advancing mechanism of the present invention using a nozzle in accordance with one aspect of the present invention.
Figure 3:
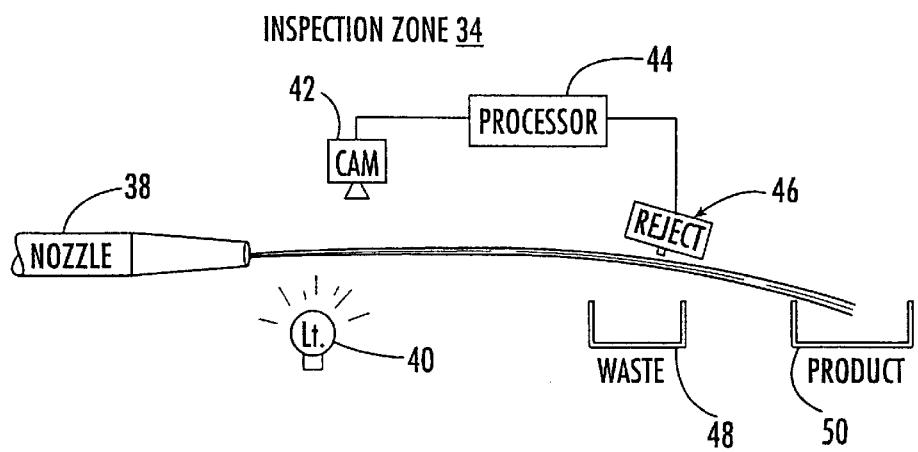
FIG. 3 is a fragmentary, side elevation view of the system of FIG. 2 and showing the nozzle of FIG. 2, a camera, and rejection mechanism.

Referring now to FIGS. 2 and 3, there is illustrated one aspect of the system and method for removing defects from citrus pulp in accordance with an embodiment showing an advancing mechanism 30 for advancing citrus pulp along a predetermined path of travel 32 into an inspection zone 34 having a citrus pulp imager, indicated generally at 36, and positioned at the inspection zone 34 for acquiring image data of the citrus pulp. In the illustrated embodiment shown in FIGS. 2 and 3, the advancing mechanism 30 includes a nozzle 38 that discharges citrus pulp along the path of travel 32 over a light source 40 that illuminates the citrus pulp from underneath the path of travel. A camera 42, as the citrus pulp imager 36, is positioned adjacent the nozzle 38 and over the citrus pulp to image the pulp as it is ejected from the nozzle into the inspection zone 34. At this time, the camera 42 acquires image data of the citrus pulp. A processor 44 is operatively connected to the camera 42 and receives the image data and processes the image data to determine defects within the citrus pulp. A rejection mechanism, indicated generally at 46 (FIG. 3), rejects any citrus pulp determined to be defective by diverting or blowing the defective citrus pulp into a waste bin 48. The final product 50 as citrus pulp is then discharged into a product bin for subsequent processing. Although different citrus pulp imagers 36 can be used in the present invention, one advantageous pulp imager is a camera 42, such as a line-scan camera or other CCD camera, for obtaining detailed pixel images with fine resolution of the citrus pulp.

The light source 40 is operative, in one aspect of the invention, for illuminating the citrus pulp at a predetermined range of wavelengths for highlighting defects to be eliminated. In one aspect of the invention, a predetermined range of wavelengths can be chosen such as to cause citrus pulp defects to fluoresce. Not only could white light be used, but different color light having different wavelengths and energies could also be used depending on the type of defect to be identified. Some of the citrus pulp defects to be detected include discolored pulp, peel or portions of peel, albedo or portions of albedo, seeds, portions of seeds, black specks, mold, or non-citrus material such as insects, insect larve or insect parts.

The processor 44 can be part of a personal computer system or larger mini or mainframe computer system as chosen by those skilled in the art. In the illustrated embodiment shown in FIG. 3, the rejection mechanism 46 could include an air rejection mechanism 52 as more clearly shown in FIGS. 6–8. FIG. 6 illustrates a bank or rack 54 of air nozzles 56 with associated valves 58 that are operatively connected to the processor 44. The imager 36 could be a bank or rack of cameras or a single camera with a large scan angle across the predetermined path of travel of the citrus pulp to obtain gray scale or other images of the citrus pulp. Using programming software known or formulated by those skilled in the art, it is possible to determine defects from changes in gray scale intensity, fluorescence, or other imaging techniques.

Once the processor 44 determines the location of the defect relative to the speed of the advancing citrus pulp, selected valves 58 are operatively turned on to allow air to blow from selected air nozzles 56 onto selected portions of the advancing citrus pulp and divert the citrus pulp determined to be defective from the predetermined path of travel, such as into the waste bin 48, as shown in FIG. 3. Each valve 58 and associated air nozzle 56 can blow air onto a given jet area "A" at a distance "D," distances and dimensions chosen by those skilled in the art, depending on the type of processing line, its speed, and type of defects most commonly encountered (FIG. 7). FIG. 8 illustrates how the air jet area "A" from each air nozzle 56 can overlap each other to ensure that all defects are removed as desired when multiple valves 58 and air nozzles 56 must be operative at once.

Figure 4:
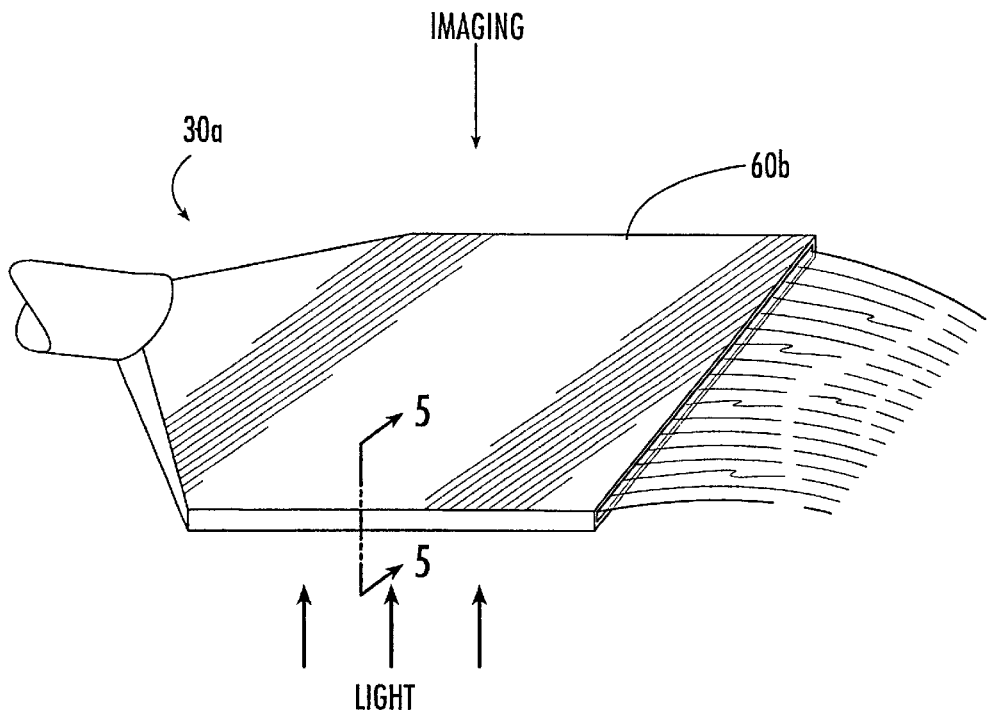
FIG. 4 is a fragmentary, isometric view of a translucent material comprising spaced translucent plates between which citrus pulp is advanced and can be imaged.
Figure 5:
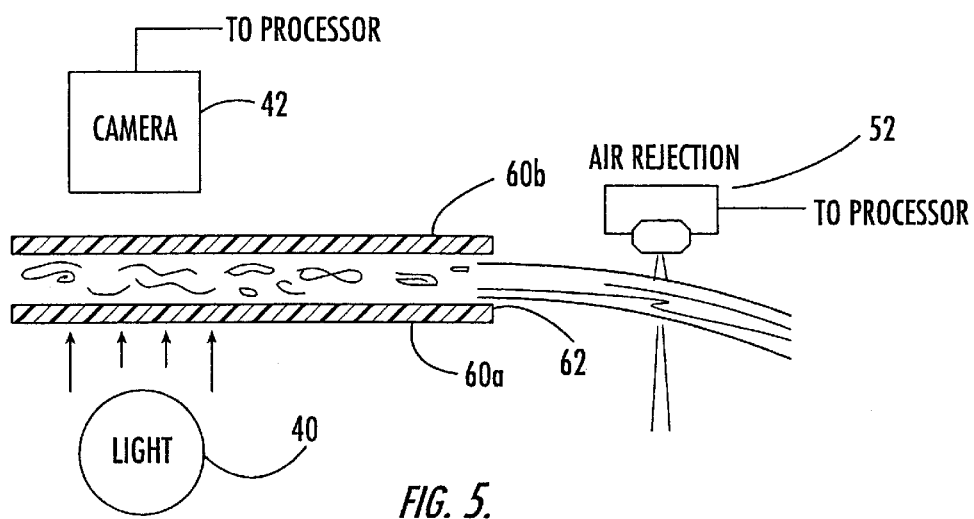
FIG. 5 is a fragmentary, side elevation view of the system for removing defects using the translucent material shown in FIG. 4 and taken along line 5—5 of FIG. 4.

FIGS. 4 and 5 illustrate another embodiment of the present invention where a second type of advancing mechanism 30a includes spaced, translucent plates 60a, 60b through which citrus pulp is advanced, such as by extruding or pumping the citrus pulp between the translucent plates to allow imaging of the citrus pulp therein. For example, the spaced translucent plates 60a, 60b could be formed from two sheets of plexiglass or glass material with side portions sealed to form a planar and elongate channel 62 as shown in FIGS. 4 and 5. A light source 40 passes light upward through the lower translucent plate 60a onto the citrus pulp that is imaged by a camera located above the upper translucent plate 60b. The processor 44 receives image data from the camera 42 and processes the image data to determine citrus pulp defects. The rejection mechanism 46, as shown in FIGS. 6–8, can be located downstream from the formed channel 62 at a known distance for applying air from nozzles onto selected portions of the citrus pulp at a predetermined time and deflecting citrus pulp determined to be defective from the citrus pulp flow.

Figure 9:
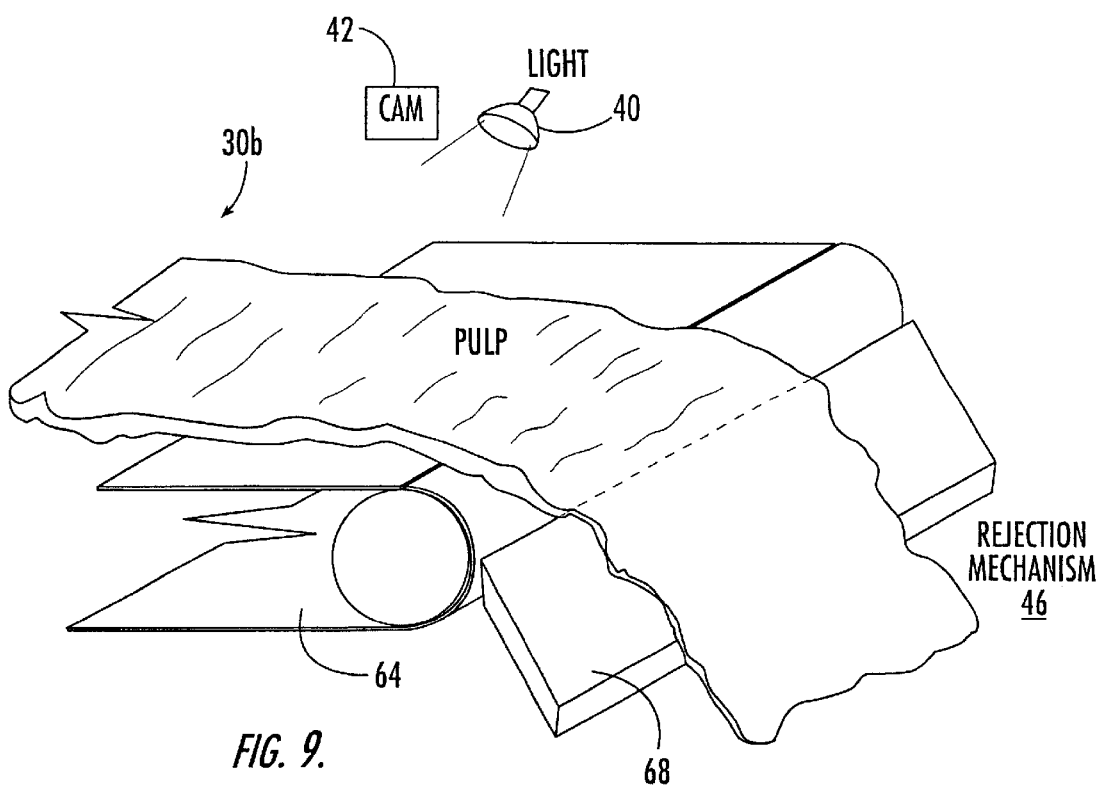
FIG. 9 is a fragmentary, isometric view of a belt conveyor that can be used for advancing citrus pulp in accordance with another aspect of the present invention.
Figure 10:
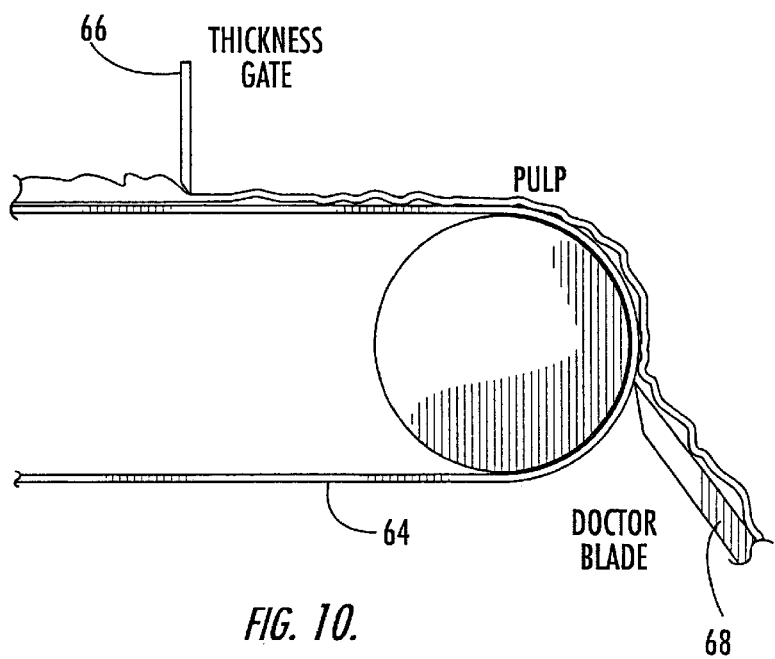
FIG. 10 is a fragmentary, side elevation view of the belt conveyor of FIG. 9 showing use of a thickness gate and doctor blade.

FIGS. 9 and 10 illustrate a third type of advancing mechanism 30b using a belt conveyor 64 that has a thickness gate 66 for distributing a predetermined thickness of citrus pulp on the belt conveyor. The citrus pulp advances along the belt conveyor 64 and past a doctor blade 68 that removes citrus pulp from the belt conveyor and passes it into a subsequent area for processing. With this type of belt system, a camera 42 could be located above the belt conveyor 64 and a light source 40 could also be located adjacent the camera 42 for illuminating the citrus pulp from above. Other known illumination systems could be used as determined by those skilled in the art. A rejection mechanism 46 is operatively associated with the belt conveyor for rejecting citrus pulp determined to be defective.

Figure 11:
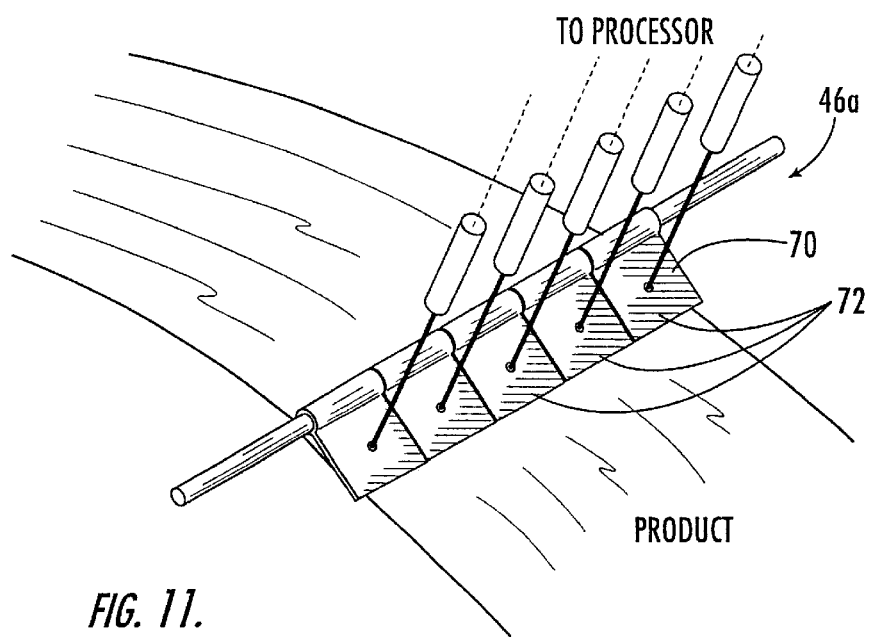
FIG. 11 is another fragmentary, isometric view of a rejection mechanism formed as a mechanical gate.
Figure 12:
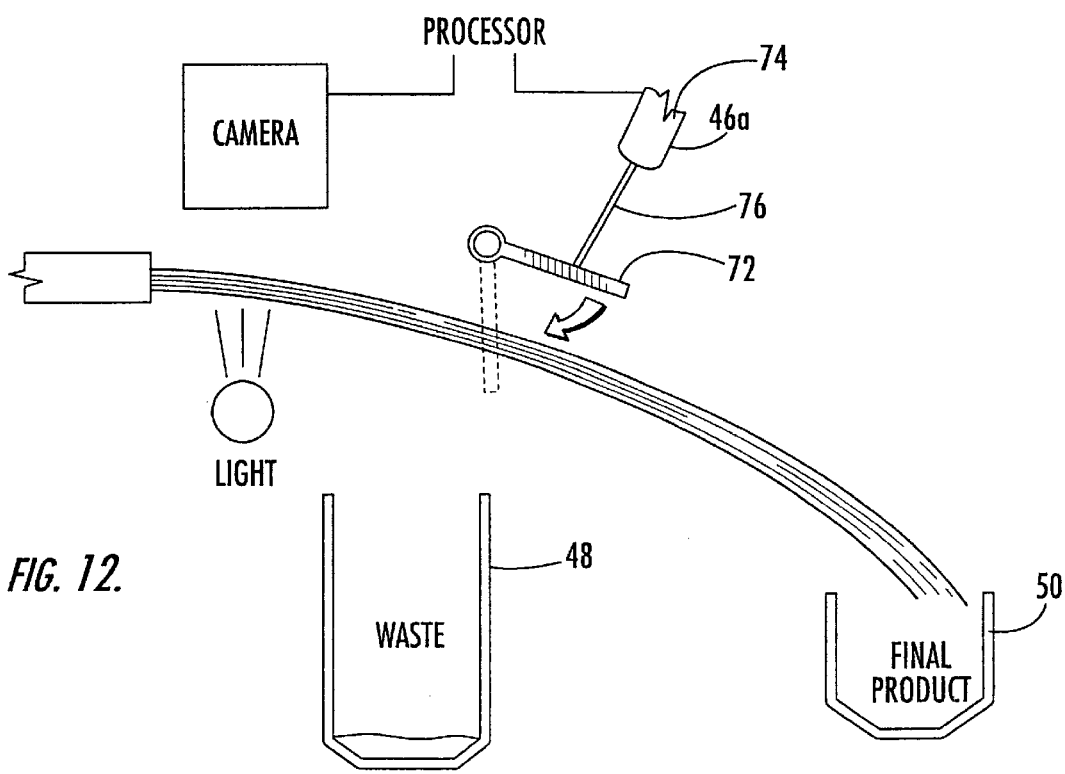
FIG. 12 is a fragmentary, side elevation view of the mechanical gate shown in FIG. 11 used with the system for removing defects from citrus pulp.

FIGS. 11 and 12 illustrate another rejection mechanism 46a that can be used as an alternative to the rack or bank of air nozzles shown in FIGS. 6–8. A mechanical gate mechanism 70 has individual gates 72 that can divert a section of citrus pulp away from a product destination into a waste bin. As shown in FIG. 12, a hydraulic, pneumatic or other power mechanism 74 operatively receives signals from the processor 44 and forces respective pistons 76 outward to divert one or more gates 72 into the citrus pulp, causing a deflection of a desired amount of citrus pulp into the waste bin 48. Naturally, if only a single defect is imaged by a camera and processed, only one piston 76 would extend for pushing one gate 72 downward for a short period of time and diverting a small portion of the citrus pulp having the one defect into the waste bin. If a large number of defects extend along a large portion of the citrus pulp flow, all gates would be deflected for a predetermined period of time.

It is evident that the present invention allows greater control over citrus pulp processing and removal of defects using image processing and machine vision technology for imaging citrus pulp at an inspection zone and acquiring image data of the citrus pulp for subsequent processing to determine defects and rejecting citrus pulp determined to be defective.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

That which is claimed is:

1. A system for removing defects from citrus pulp comprising:
   an advancing mechanism that receives citrus pulp and forms a substantially planar flow of citrus pulp of predetermined thickness and advances the citrus pulp along a predetermined path of travel into an inspection zone;
   a citrus pulp imager positioned at the inspection zone for acquiring image data of the citrus pulp;
   a processor operatively connected to said citrus pulp imager for receiving the image data and processing the image data to determine defects within the citrus pulp; and
   a rejection mechanism for rejecting any citrus pulp determined to be defective.

2. A system according to claim 1, wherein said citrus pulp imager further comprises a light source for illuminating the citrus pulp at the inspection zone and a camera located at the inspection zone for acquiring images of the citrus pulp.

3. A system according to claim 2, wherein said light source is operative for illuminating the citrus pulp at a predetermined range of wavelengths for highlighting defects to be illuminated.

4. A system according to claim 3, wherein the predetermined range of wavelengths is such as to cause defects to fluoresce.

5. A system according to claim 1, wherein said advancing mechanism comprises a belt conveyor, nozzle or translucent material through which citrus pulp is advanced and imaged.

6. A system according to claim 1, wherein said rejection mechanism comprises a mechanical diverter that diverts any citrus pulp determined to be defective from the path of travel.

7. A system according to claim 1, wherein said rejection mechanism comprises at least one air nozzle for blowing air onto citrus pulp determined to be defective and diverting the defective citrus pulp from the path of travel.

8. A system according to claim 1, wherein said processor is operative for determining defects including discolored pulp, peel or portions of peel, albedo or portions of albedo, seeds, portions of seeds, black specks, mold, non-citrus material including insects, insect larvae or insect parts.

9. A method of removing defects from citrus pulp comprising the steps of:
   receiving citrus pulp at an advancing mechanism and forming thereat a substantially planar flow of citrus pulp of predetermined thickness while advancing the citrus pulp along a predetermined path of travel into an inspection zone;
   imaging the citrus pulp at the inspection zone to acquire image data of the citrus pulp;
   processing the image data to determine defects within the citrus pulp; and
   rejecting any citrus pulp determined to be defective.

10. A method according to claim 9, wherein the step of imaging further comprises the step of illuminating the citrus pulp at the inspection zone and acquiring images from a camera located at the inspection zone.

11. A method according to claim 10, and further comprising the step of illuminating the citrus pulp at a predetermined range of wavelengths for highlighting defects to be imaged.

12. A method according to claim 11, and further comprising the step of illuminating the citrus pulp at a predetermined range of wavelengths to cause defects to fluoresce.

13. A method according to claim 9, wherein the step of advancing citrus pulp further comprises the step of conveying citrus pulp into the inspection zone by one of conveying along a belt conveyor, discharging through a nozzle, or extruding or pumping through a translucent material to allow imaging of the citrus pulp therein.

14. A method according to claim 9, wherein the step of rejecting any citrus pulp determined to be defective comprises the step of diverting any citrus pulp determined to be defective from the path of travel to remove any defective citrus pulp.

15. A method according to claim 14, wherein the step of diverting the citrus pulp from the path of travel further comprises the step of blowing any citrus pulp away from the path of travel.

16. A method according to claim 14, wherein the step of diverting the citrus pulp further comprises the step of mechanically engaging and diverting the citrus pulp determined to be defective away from the path of travel.

17. A method according to claim 9, wherein the step of determining defects further comprises the step of determining discolored pulp, peel or portions of peel, albedo or portions of albedo, seeds, portions of seeds, black specks, mold, non-citrus material including insects, insect larvae or insect parts.

* * * * *